(12) United States Patent
Oishi (10) Patent No.: US 9,770,178 B2
(45) Date of Patent: Sep. 26, 2017

(54) BLOOD PRESSURE MEASURING CUFF

(75) Inventor: Teishi Oishi, Tokyo (JP)

(73) Assignee: Nihon Kohden Corporation, Tokyo (JP)

( * ) Notice: Subject to any disclaimer, the term of this patent is extended or adjusted under 35 U.S.C. 154(b) by 673 days.

(21) Appl. No.: 13/596,727

(22) Filed: Aug. 28, 2012

(65) Prior Publication Data

US 2013/0053710 A1 Feb. 28, 2013

(30) Foreign Application Priority Data

Aug. 29, 2011 (JP) .................................. 2011186515

(51) Int. Cl.
*A61B 5/02* (2006.01)
*A61B 5/022* (2006.01)
*A61B 5/021* (2006.01)

(52) U.S. Cl.
CPC ............ *A61B 5/02233* (2013.01); *A61B 5/02* (2013.01); *A61B 5/02141* (2013.01)

(58) Field of Classification Search
CPC .............................. A61B 5/02; A61B 5/02141
USPC ........................................................ 600/499
See application file for complete search history.

(56) References Cited

U.S. PATENT DOCUMENTS

| 2,717,437 | A | | 9/1955 | De Mestral | |
| 3,312,583 | A | * | 4/1967 | Rochlis .............. | A44B 18/0049 15/187 |
| 5,243,991 | A | * | 9/1993 | Marks ........................... | 600/499 |
| 6,149,600 | A | * | 11/2000 | Poorman-Ketchum ....... | 600/499 |
| 6,224,558 | B1 | * | 5/2001 | Clemmons ..................... | 600/490 |
| 6,290,653 | B1 | * | 9/2001 | Che ..................... | A61B 5/02233 600/490 |
| 7,478,460 | B2 | * | 1/2009 | Gallant et al. .................. | 24/452 |
| 8,517,952 | B2 | * | 8/2013 | Nakanishi et al. ........... | 600/499 |
| 2002/0162197 | A1 | * | 11/2002 | Romanko .......... | A44B 18/0003 24/306 |
| 2003/0031386 | A1 | * | 2/2003 | Shepard ............. | A44B 18/0084 383/61.1 |
| 2003/0155054 | A1 | * | 8/2003 | Bell .................... | B60C 23/0493 152/151 |

(Continued)

FOREIGN PATENT DOCUMENTS

EP 2258259 A1 12/2010
JP 4157148 B1 9/2008

(Continued)

OTHER PUBLICATIONS

Office Action dated Jul. 14, 2015, and English Language Translation Thereof, from State Intellectual Property Office of People's Republic of China, Application No. 201210308566.1.

(Continued)

*Primary Examiner* — Jacqueline Cheng
*Assistant Examiner* — Puya Agahi
(74) *Attorney, Agent, or Firm* — Drinker Biddle & Reath LLP (57) ABSTRACT

A blood pressure measuring cuff includes: a belt-like body wrapped around a blood pressure measuring site of a patient; a hook surface provided on one surface of the body and having a hook structure; and a hook surface provided on the other surface of the body and having a hook structure. When the body is wrapped around the blood pressure measuring site of the patient, the hook surface and the hook surface mutually fix each other.

5 Claims, 9 Drawing Sheets

(56) References Cited

U.S. PATENT DOCUMENTS

| | | |
|---|---|---|
| 2004/0049114 A1 | 3/2004 | Alesse |
| 2008/0119744 A1* | 5/2008 | Yang et al. .................. 600/490 |
| 2009/0010735 A1* | 1/2009 | Gallant et al. ............... 411/510 |
| 2010/0121205 A1 | 5/2010 | Nakanishi et al. |
| 2010/0168527 A1 | 7/2010 | Zumo et al. |
| 2011/0092829 A1* | 4/2011 | Hu ........................ A61B 5/022 |
| | | 600/490 |

FOREIGN PATENT DOCUMENTS

| | | |
|---|---|---|
| JP | 2010279470 A | 12/2010 |
| WO | WO-2010135216 A1 | 11/2010 |

OTHER PUBLICATIONS

Official Notice of Reason for Refusal dated Jan. 5, 2016, and English translation thereof, for Japanese Patent Application No. 2012-182617.

Office Action dated Jan. 20, 2016, and English translation thereof, from State Intellectual Property Office of the People's Republic of China, Application No. 2012-10308566.1.

* cited by examiner

BLOOD PRESSURE MEASURING CUFF

CROSS-REFERENCE TO RELATED APPLICATIONS

This application claims benefit to Japanese Application No. 2011-186515, filed Aug. 29, 2011. The aforementioned priority application is incorporated herein by reference in its entirety.

TECHNICAL FIELD

The present invention relates to a blood pressure measuring cuff which prevents loosening of the cuff upon blood pressure measurement.

DESCRIPTION OF RELATED ART

Recent blood pressure measurement generally adopts a pressure measurement by a step-down deflating scheme. In the step-down deflating scheme, first, a pressure of cuff wrapped around the arm is raised to a maximum blood pressure or more. Next, pressure oscillation due to pulsation generated in the cuff is detected when the blood pressure gradually deflates. And, a blood pressure value etc. are calculated based on the detection. In the step-down deflating scheme, the cuff pressure is inflated to the pressure, for example to 180 mmHg, higher than a normal maximum blood pressure so that the maximum blood pressure can be measured. According to such scheme, the problem of increasing load on the arm exists.

By contrast with this, a blood pressure monitor of a linear inflating scheme is developed. According to the linear inflating scheme, the blood pressure is measured while the pressure of a cuff is linearly inflated. Air is filled in an air bag upon pressure inflating and the cuff tightens the arm harder. Due to this, a shearing force of releasing a fixing of a hook-and-loop fastener, which fixes the cuff, acts in a circumferential direction of the fastener.

The shearing force causes phenomena that the hook-and-loop fastener of the cuff is misaligned from a peeling start side in the circumferential direction and that fixing of a hook surface and a loop surface forming the hook-and-loop fastener is released. Due to, for example, the above loosening of the cuff, a peeling sound of the hook-and-loop fastener generated and an oscillation is generated from the cuff. Oscillation due to, for example, loosening of the cuff is different from oscillation due to the blood flow. Therefore, when loosening of the cuff occurs, an oscillatory waveform due to loosening of the cuff is superimposed on an oscillatory waveform due to the blood flow as noise, and the measurement accuracy may be reduced or measurement failure may be caused.

In order to prevent noise due to loosening of the cuff, Japanese Patent No. 4157148 discloses a tightening belt which reduces the diameter of a cuff. The Japanese Patent also discloses a cushion member on at least one surface of surfaces which of one end and the other end of the cuff grind each other. The cushion member is provided in an area where the tightening belt overlaps.

The blood pressure monitor in the Japanese Patent has, for example, the tightening belt, a knob, a metal base through which the tightening belt passes and an open lever in the outer periphery of the cuff. A plurality of above members project on the outer side of the cuff. Therefore, when a cuff is attached in an operating room, the cuff is tangled with wirings such as tubes which have already been attached to a patient. And, the cuff is likely to remove the wiring. Further, with the cuff in the Japanese Patent, it is necessary to pass the tightening belt into the base, and determine a tightening state by using a knob. In case of emergency as in an operating room, an operation of passing the tightening belt into the base is bothersome. And, fixing a cuff is not easy.

SUMMARY

This present invention provides a blood pressure measuring cuff which prevents loosening of the cuff and allows the cuff to be easily attached and detached.

A blood pressure measuring cuff includes a belt-like body, a first hook surface and a second hook surface. The belt-like body is configured to wrap around a blood pressure measuring site of a patient. The first hook surface is provided on one surface of the body and has a hook structure. The second hook surface is provided on another surface of the body and has a hook structure. According to an aspect of the present invention, when the body is configured to wrap around the blood pressure measuring site of the patient, the first hook surface and the second hook surface mutually fix each other.

DETAILED DESCRIPTION

An embodiment of the present invention will be described with reference to the accompanying drawings below. In addition, the following disclosure by no means limits significance of a technical scope and terms described in the claims. Further, dimensional ratios of the drawings are exaggerated for the sake of description, and are different from actual ratios in some cases.

Figure 1:
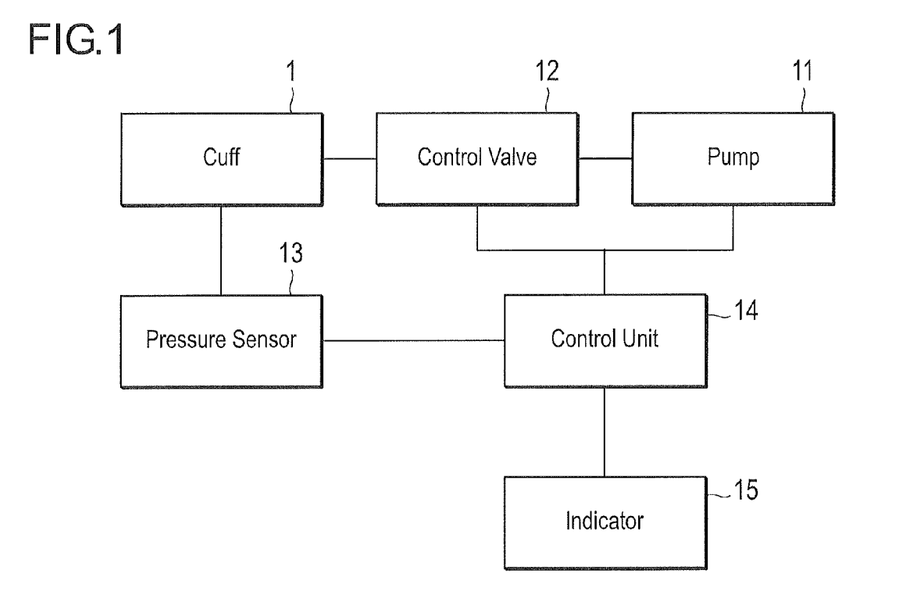
FIG. 1 is a block diagram according to an embodiment of the present invention.
Figure 2:
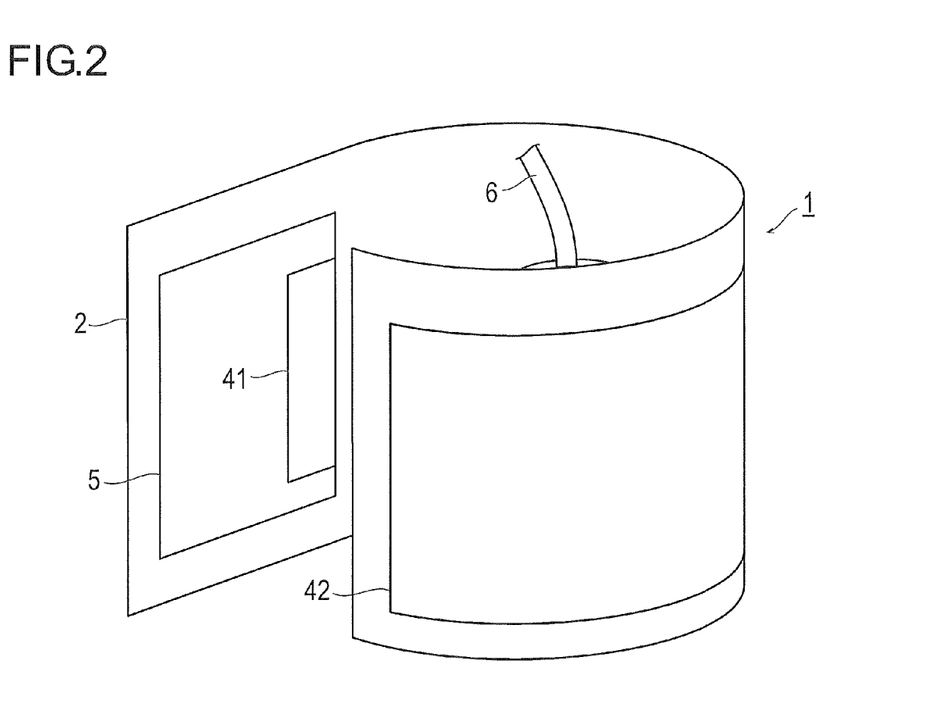
FIG. 2 is a perspective view of a blood pressure measuring cuff according to an embodiment of the present invention.

FIG. 1 is a block diagram of a blood pressure monitor using a cuff according to the present embodiment, and FIG. 2 is a perspective view of a blood pressure measuring cuff according to the present embodiment. The blood pressure monitor according to the present embodiment is an oscillometric electronic blood pressure monitor. And the blood pressure monitor calculates, for example, a maximum blood pressure and a minimum blood pressure by processing a waveform acquired upon inflating the cuff. The blood pressure monitor has a pump 11, a control valve 12, a pressure sensor 13, a control unit 14 and an indicator 15.

The pump 11 supplies a predetermined flow rate of air to a cuff 1. The control valve 12 is closed by the control unit 14 when an operation starts. The pressure sensor 13 detects a pressure of the arm upon the cuff being inflated by the pump 11, and sends a pressure signal to the control unit 14. The control unit 14 computes a value of a pressure which is applied to the arm, based on a current arm pressure acquired from the pressure sensor 13. And the control unit 14 controls the flow rate of the pump 11. When blood measuring processing is finished, the control unit 14 opens the control valve 12, and stops the pump 11. The indicator 15 displays various results such as the maximum blood pressure and the minimum blood pressure computed by the control unit 14.

In FIG. 2, the cuff 1 has a body 2 of the blood pressure measuring cuff, an air bag 3, and hook surfaces 41, 42 and a loop surface 5 forming a hook-and-loop fastener. The body 2 is made of, for example, plastic fiber such as polyester or nylon, and its outer periphery is fixed by way of sewing. The body 2 is formed in a belt shape (a rectangular shape) when expanded.

The outer periphery of the body 2 is in a state where a part of the outer periphery is not sewn to allow the air bag 3 to be accommodated. Further, a tube 6 from the body of the blood pressure monitor is allowed to project from a portion which is not sewn.

Figure 3:
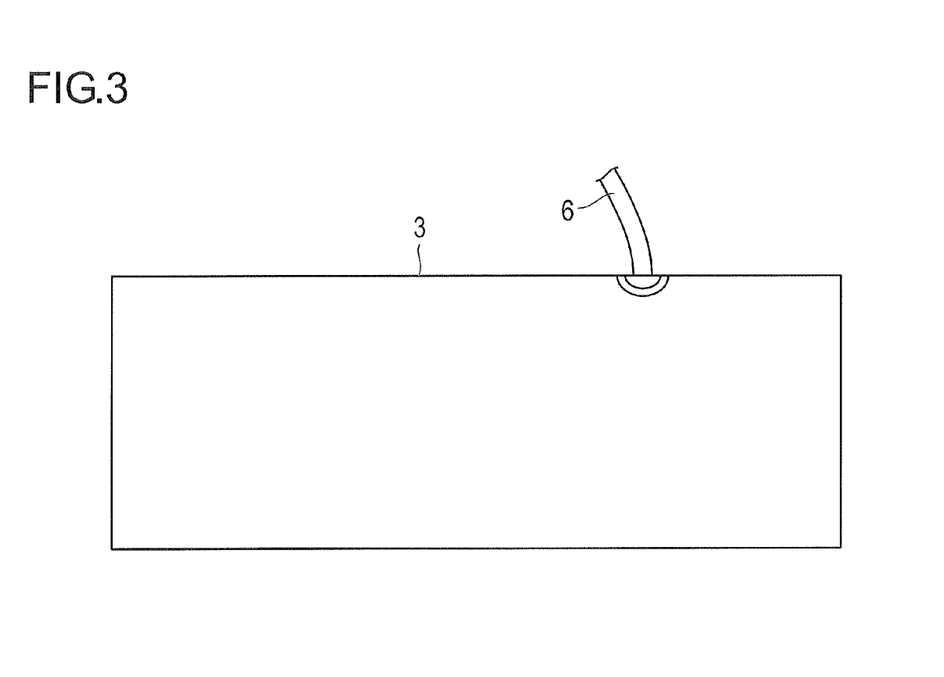
FIG. 3 is a plan view of an air bag.

FIG. 3 is a view illustrating the air bag 3. The air bag 3 has substantially the same shape as the body 2. The air bag 3 is accommodated in the body 2 from the portion of the outer periphery of the body 2 which is not sewn by such means as bending the air bag 3. The tube 6 is jointed to one side of the air bag 3. The tube 6 connects various configurations such as the cuff 1 and the pressure sensor 13 in the blood pressure monitor.

Figure 4:
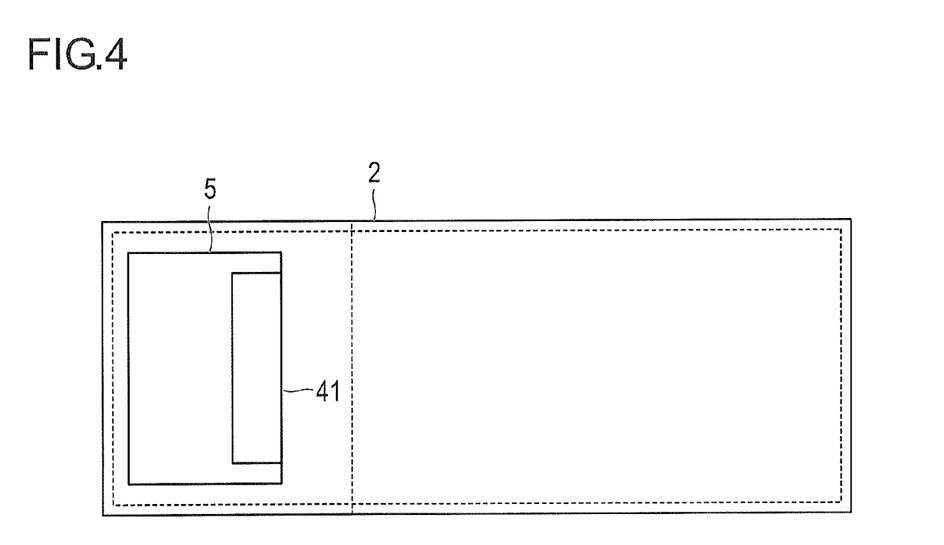
FIG. 4 is a plan view when the cuff is expanded.
Figure 5:
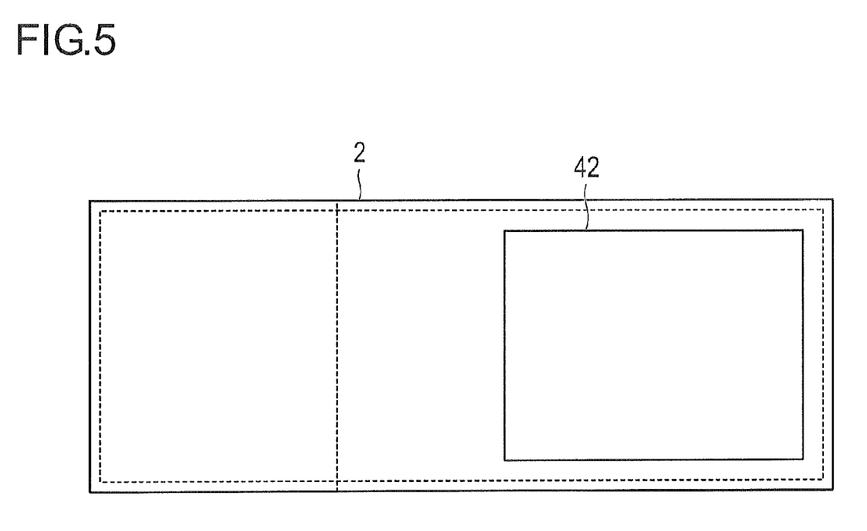
FIG. 5 is a plan view when the cuff in FIG. 4 is seen from an opposite direction.

FIG. 4 is a plan view seen from one surface with expanding the cuff, and FIG. 5 is a plan view of the cuff seen from the opposite surface of FIG. 4. As illustrated in FIGS. 2 to 4, the hook surface 41 and the loop surface 5 forming the hook-and-loop fastener is a fixing means for the cuff 1. And, the hook surface 41 and the loop surface 5 are provided on a surface different from the hook surface 42. The hook surfaces 41 and 42 are made of the same roll member. When wrapped around the arm, the hook surface 41 is on the inner side and the hook surface 42 is on the outer side.

The hook surfaces 41, 42 and the loop surface 5 of the required amount are cut from the roll member, and sewn to the body 2.

When the cuff 1 is wrapped around a blood pressure measuring site such as the arm, the loop surface 5 and the hook surface 42 are sewn to an end of each surface of the body 2 in the longitudinal direction so that the loop surface 5 and the hook surface 42 can be fixed facing each other. The hook surface 42 is formed longer than the loop surface 5 in the circumferential direction to support individual differences of arm circumferential length when wrapped around arm of patients. The hook surface 42 and the loop surface 5 are formed to have the same width in the width direction of the body 2.

As illustrated in FIGS. 2 and 4, the hook surface 41 is arranged at a position of a peeling start side on which the hook-and-loop fastener is peeled off from the arm. Further, as illustrated in FIGS. 2 and 4, the length of the hook surface 41 is adjusted so that the loop surface 5 is arranged on both sides of the width direction of the body 2. The hook surface 41 is sewn on the loop surface 5. The hook surface 41 is spaced farther apart from the body 2 than the loop surface 5 in the present embodiment.

Next, blood pressure measurement using the cuff 1 according to the present embodiment will be described. The cuff 1 is wrapped around and attached to one of left or right brachial part of a patient upon blood pressure measurement. Next, the cuff 1 which includes the air bag is inflated by the pump 11. The cuff 1 according to the present embodiment acquires an oscillation waveform upon cuff inflation. Since the cuff 1 is inflated, the shearing force to release fixing of the fastener acts on the hook-and-loop fastener portion of the cuff 1 in a circumferential direction of the arm.

In this case, there is a concern that fixing of the hook surface and the loop surface forming the hook-and-loop fastener is slightly released a little by little. Even when fixing of the hook surface and the loop surface are slightly released, the above peeling sound and oscillation occur. And, the oscillation waveform by the peeling is superimposed on the oscillation waveform by blood flow as noise.

Factors which cause the noise include loosening of a cuff, peeling of the hook-and-loop fastener, and friction between an air bag and the cuff. The main factor which causes the noise is thought to be due to loosening of the hook-and-loop fastener.

Therefore, it is necessary for the linear inflating scheme to prevent fixing of the hook-and-loop fastener portion from being released upon cuff inflation.

Figure 6:
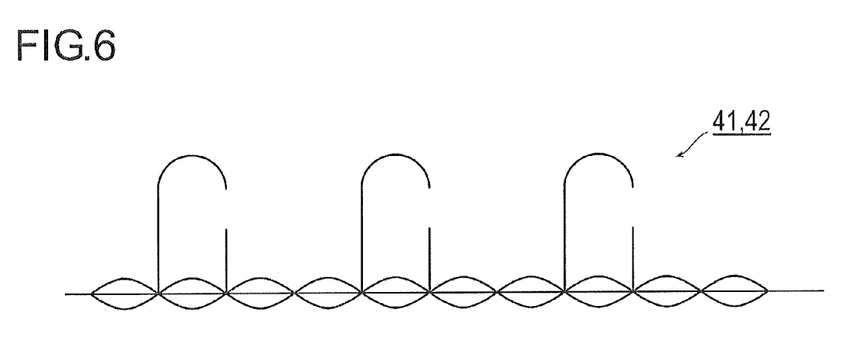
FIG. 6 is an enlarged view of a hook surface forming a hook-and-loop fastener.
Figure 7:
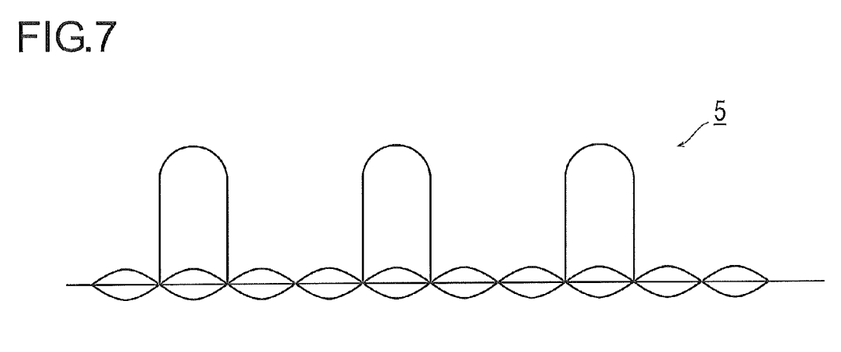
FIG. 7 is an enlarged view of a loop surface forming a hook-and-loop fastener.

FIG. 6 is an enlarged view of a hook shape forming the hook surface, and FIG. 7 is an enlarged view of a loop shape forming the loop surface. The hook surface forming the hook-and-loop fastener has an infinite number of key-shaped structures (hook structures) as illustrated in FIG. 6. On the other hand, the loop surface has an infinite number of loop structures as illustrated in FIG. 7.

Forces produced by the hook-and-loop fastener can be classified roughly into a force vertical to the hook-and-loop surface and a shearing force along the hook-and-loop fastener. Generally speaking, a combination of the hook surface and the loop surface seems to provide a harder fixing force against the vertical direction force and the shearing force than other combinations of the hook surface and the loop surface. However, it has become clear that a combination of the hook surfaces has a harder fixing force against the shearing force than the combination of the hook surface and the loop surface.

Therefore, by providing the hook surfaces 41 and 42 on both surfaces of the cuff 1, it is possible to oppose to the shearing force which is difficult to be opposed only by the combination of the hook surface 42 and the loop surface 5. By this means, it is possible to prevent loosening of the cuff and secure the measurement accuracy of the linear inflating scheme.

Further, the cuff according to the present embodiment adopts a conventional hook-and-loop fastener. Therefore, the cuff does not require a complicated operation and can be easily wrapped to the arm of a patient.

Furthermore, the cuff pressure upon cuff inflation is monitored with the linear inflating scheme. Therefore, it is not necessary to inflate the cuff pressure more than necessary and it is possible to reduce the burden on the arm of a patient.

Still further, it is necessary with the step-down deflating scheme to perform measurement waiting for cuff inflation to end. However, if it is possible to perform measurement upon cuff inflation, such time loss is not produced and it is possible to quickly perform measurement.

Consequently, by utilizing the cuff 1 according to the present embodiment, it is possible to finish measuring the blood pressure in a shorter time than a conventional measuring with the step-down deflating scheme while maintaining the measurement accuracy. And it is also possible to reduce a physical burden on a patient.

The cuff 1 has a belt shape (rectangular shape) when expanded as illustrated in FIGS. 4 and 5. Therefore, it is not necessary to distinguish cuffs for left and right arms compared to a conical cuff when the cuff is expanded. The cuff can be easily attached to the arm.

Examples

Next, a result of an endurance test of the cuff according to the present embodiment will be described.

This test is an open/close test (opening/closing test) of a cuff. In this test, a cuff is attached to a pseudo-arm. After the pressure is inflated from 0 to 300 mmHg and the pressure is released, the cuff is then removed from the pseudo-arm. Further, the above operation is performed in units of 100 times to acquire output data. After the operation is finished, a condition of a noise waveform is checked while checking a waveform.

As the present example, the cuff according to the present invention has a hook surface and a loop surface on one surface and also has a hook surface on the other surface. Further, As a comparative example, the following test was conducted using a conventional cuff having only the hook surface on one surface and only the loop surface on the other surface.

Figure 8:
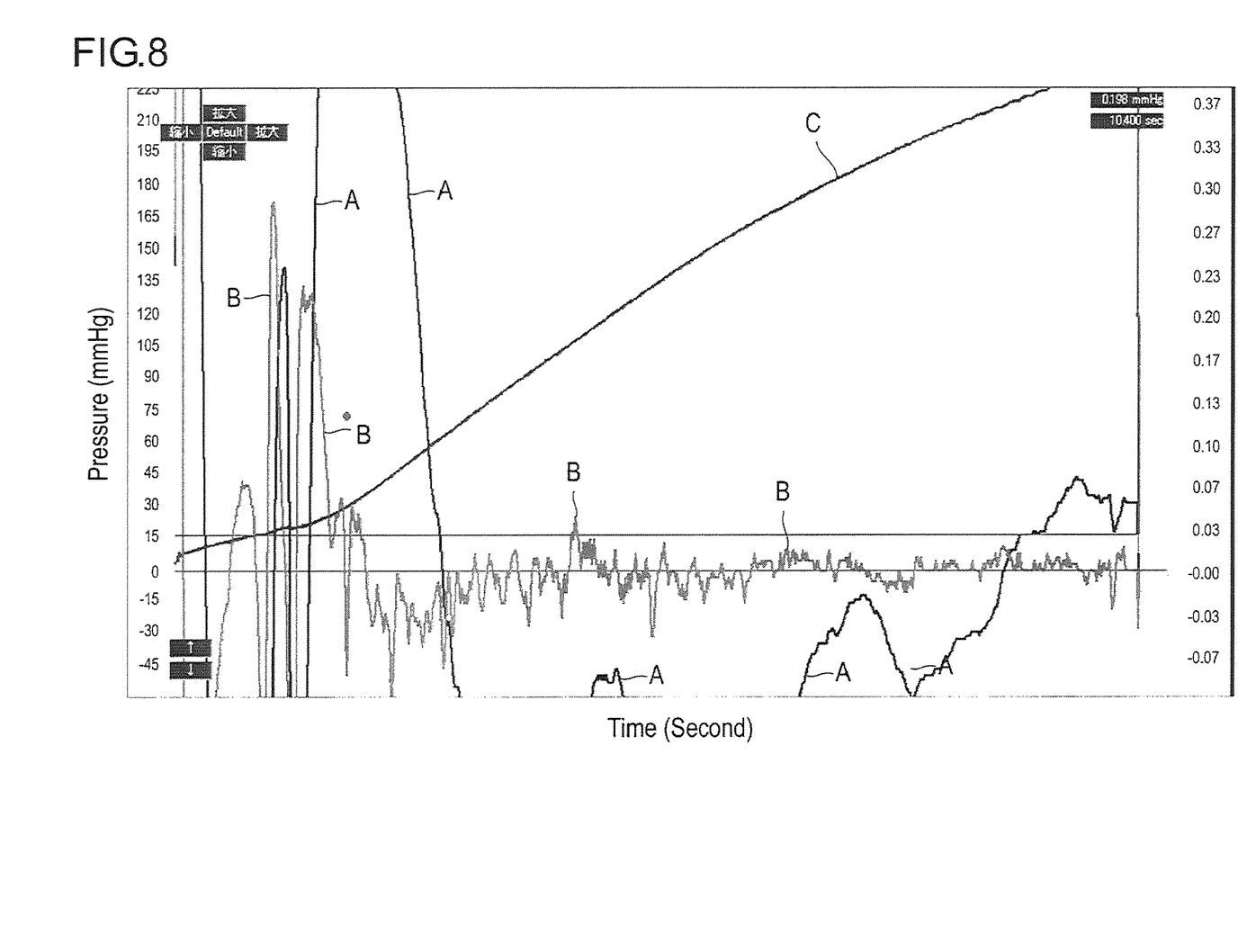
FIG. 8 is a waveform diagram illustrating that a blood pressure is measured by a linear inflating scheme using a cuff according to an embodiment of the present invention without performing an opening/closing test.
Figure 9:
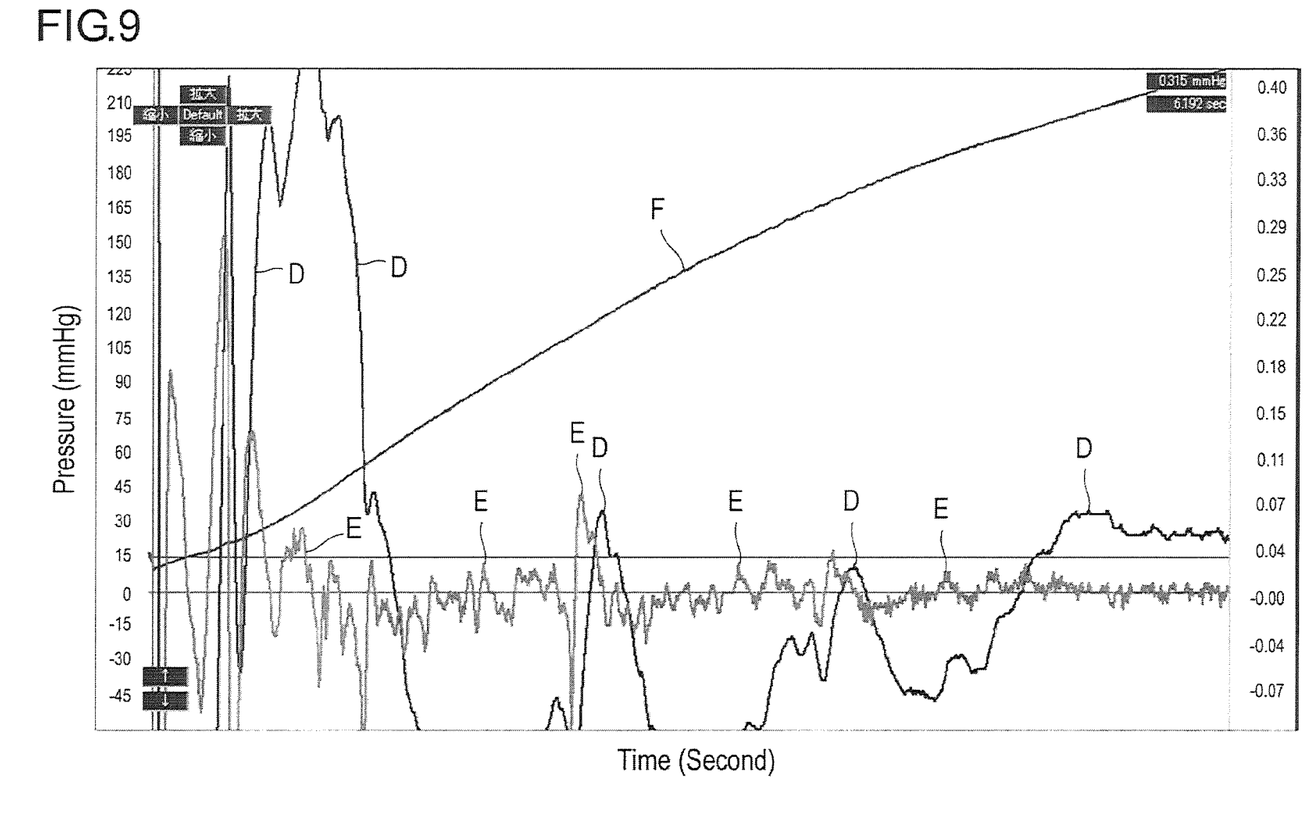
FIG. 9 is a waveform diagram illustrating that a blood pressure is measured by a linear inflating scheme after performing an opening/closing test 500 times using a cuff according to an embodiment of the present invention.
Figure 10:
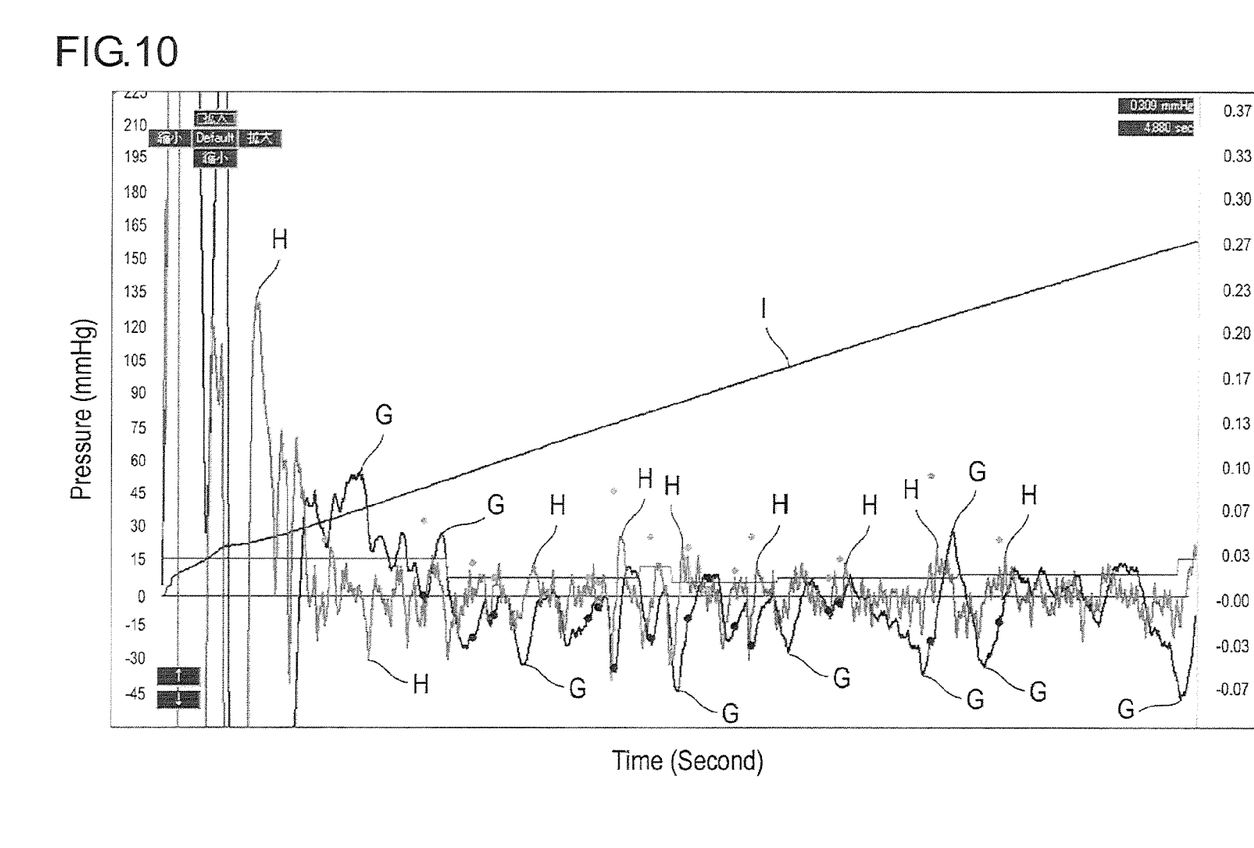
FIG. 10 is a waveform diagram illustrating that a blood pressure is measured by a linear inflating scheme without performing an opening/closing test using a conventional cuff.
Figure 11:
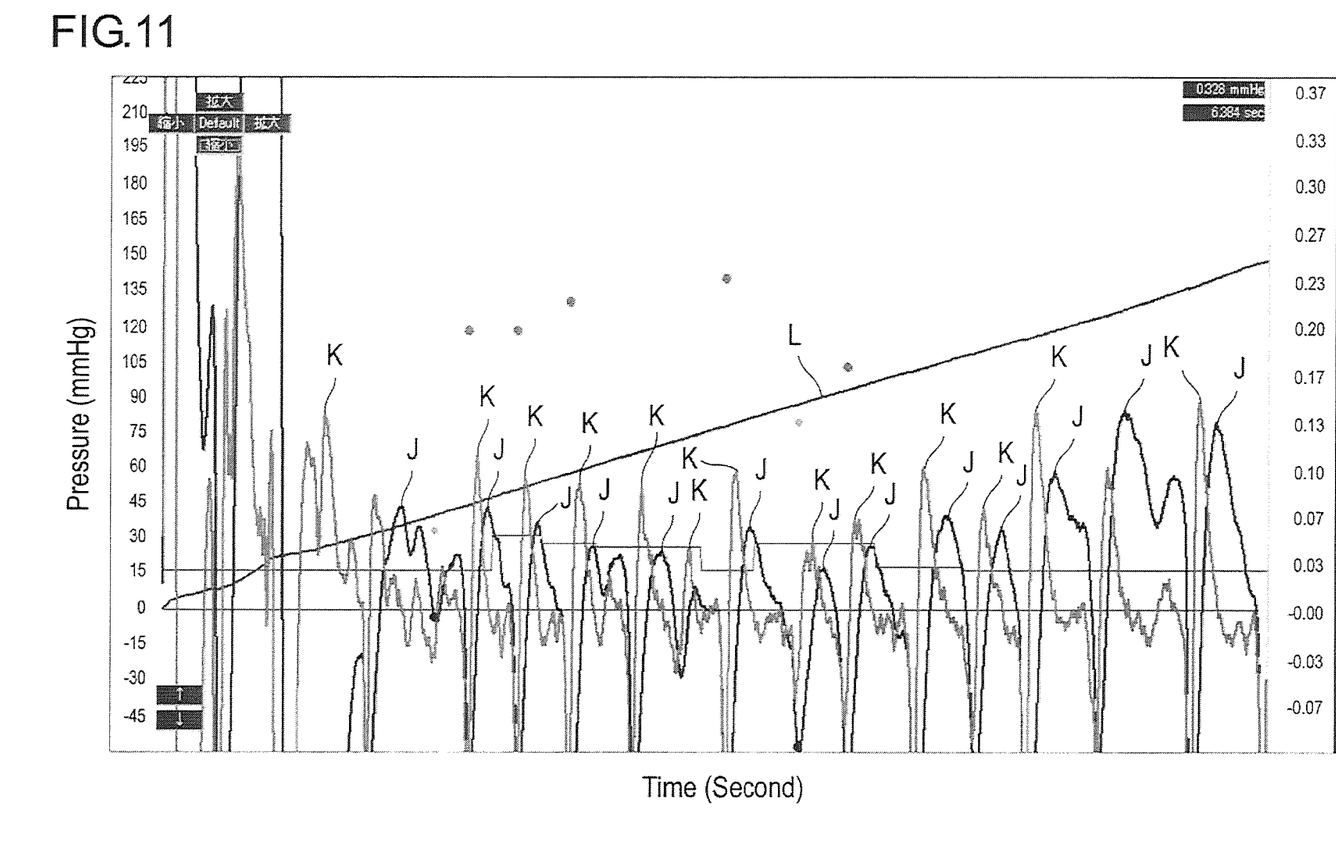
FIG. 11 is a waveform diagram illustrating that a blood pressure is measured by a linear inflating scheme after performing an opening/closing test 500 times using a conventional cuff.

FIG. 8 is a waveform diagram when a blood pressure is measured by using a cuff of the present example in a state that it has been conducted an opening/closing test 0 time, namely, in a state of new cuff. FIG. 9 is a waveform diagram when a blood pressure is measured according to a linear inflating scheme after the opening/closing test is conducted 500 times. FIG. 10 is an oscillation waveform diagram in a state where an opening/closing test is not conducted using a conventional cuff as a comparative example. FIG. 11 is a waveform diagram when a blood pressure is measured after an opening/closing test is conducted 500 times using a conventional cuff.

In FIGS. 8 to 11, waveforms A, D, G and J are oscillation waveforms, and pulsation is recognized based on these oscillation waveforms. Waveforms B, E, H and K are differential waveforms of the waveforms A, D, G and J. That is, the waveforms B, E, H and K are obtained by first derivation of the oscillation waveforms, and represent noise components. Waveforms C, F, I and L represent pressure waveforms upon cuff inflation by using a pump.

In FIGS. 8 to 11, when the amplitudes of the waveforms B, E, H and K are greater, noise is more significant. As is clear upon comparison of FIGS. 8 and 9, with the cuff according to the present example, even when an opening/closing test is conducted 500 times, it is possible to confirm that the amplitude of noise components hardly changes and measurement accuracy is good.

By contrast with this, in case of a conventional cuff, when an opening/closing test is conducted 500 times as illustrated in FIGS. 10 and 11, it is possible to confirm that the amplitude of noise components becomes significant and the measurement accuracy decreases.

Upon comparison of FIGS. 9 and 11, periodical noise occurs in FIG. 11 which is not observed in FIG. 9. The cuff according to the comparative example is not provided with a hook surface on the loop surface side as in the present example, and periodical noise occurs. That is, it is supposed that a conventional cuff is repeatedly fixed and released and the loop surface is damaged, and therefore fixing of the hook surface and the loop surface is gradually released and periodical noise occurs as illustrated in FIG. 11.

By using the cuff according to the present example, it is also possible to oppose strongly to a shearing force against conventional weak fixing of hook surface and a loop surface. The present example makes it possible to suppress occurrence of noise due to release of the fastener and to secure the measurement accuracy. As described above, the actual test result shows that the measurement accuracy of the linear inflating scheme is sufficiently secured by the cuff according to the present example.

Modification

A modification of the embodiment is as follows. Any one of the surfaces on which a hook surface is provided is desirably provided with not only the hook surface but also one or more loop surfaces. The hook surfaces are more robust against the shearing force than the combination of the hook surface and the loop surface. On the other hand, the hook surfaces are weaker against the force vertical to the surface than the combination of the hook surface and the loop surface.

Thus, by providing the loop surface on one of the hook surfaces, it is possible to oppose to not only the shearing force but also the force vertical to the surface. Therefore, it is possible to prevent cuff loose strongly.

Further, when release of fixing of the hook surface and the loop surface is started once, even if the hook surfaces are arranged in an upstream and a midstream, it is not easy to stop releasing of the fixing. Therefore, when both the hook surface and the loop surface are provided on one side, it is possible to effectively prevent loosening of the cuff by arranging the hook surface on a peeling start side of the hook-and-loop fastener as illustrated in FIG. 2. Here, "the peeling start side" refers to a side on which peeling of the hook-and-loop fastener is started when a shearing force, on the hook-and-loop fastener fixed to the arm, is applied in a circumferential direction of the arm.

Further, at the peeling start position of the hook surface, it is desirable to provide not only the hook surface but also the loop surface 5 on both sides of the hook surface 41 in the width direction of the body 2 as illustrated in FIGS. 2 and 4. As described above, it is possible to oppose to the shearing force by arranging the hook surface on the peeling start side. However, the hook surface is comparatively weak against the force vertical to the surface. Consequently, by providing the loop surface and the hook surface at the peeling start position, it is possible to reliably prevent start of peeling and prevent loosening of the cuff strongly.

Further, it is desirable for the hook surface provided together with the loop surface that a longer side rather than shorter side of the hook surface 41 is arranged on the peeling start side as illustrated in FIGS. 2 and 4. With the conventional hook-and-loop fastener, the force opposing to the shearing force is comparatively insufficient. Therefore, it is possible to effectively prevent cuff loose intensively against the shearing force by arranging the longer side of the hook surface on the peeling start side.

Further, the hook surface is desirably spaced farther apart from the body than the loop surface. That is, when the cuff is wrapped around the arm, the hook surface is desirably provided at a higher position than the loop surface in the radial direction.

According to the above positional relationship, even when both of the hook surface and the loop surface are arranged, the hook surface always contacts another hook surface upon fixing. Consequently, it is possible to reliably fix the hook surfaces, and prevent loosening of the cuff. Further, when the hook surfaces and the loop surface are aligned and arranged, it is possible to achieve the same effect as abovementioned by elongating hooks of the hook surfaces, and positioning hooks of the hook surfaces upon wrapping around arm to 1 to several millimeters higher position than the loop surface in the radial direction.

Furthermore, it is possible to sufficiently oppose to the shearing force or the vertical direction force applied to the cuff by using the cuff according to the modification. Consequently, it is possible to reduce a contact area of the hook surfaces and the loop surface which are required for fixing.

Figure 15:
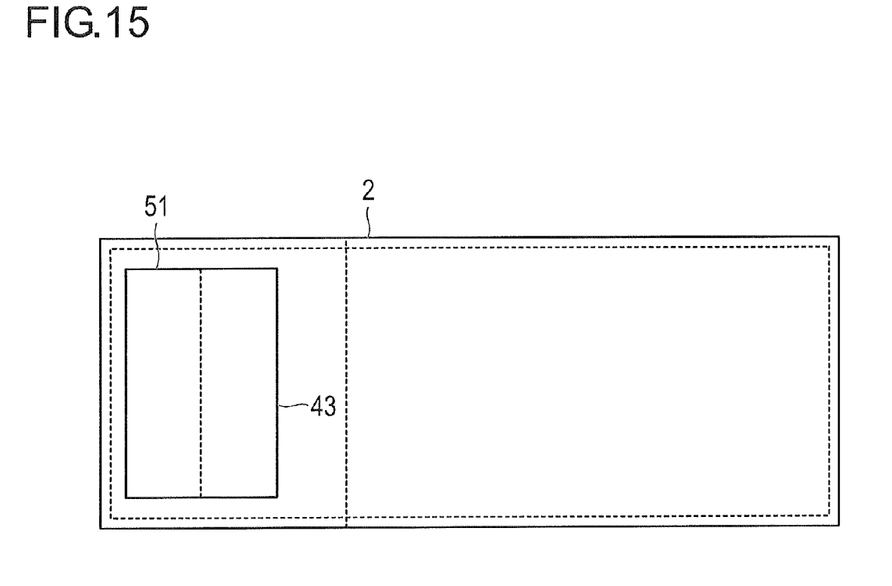
FIG. 15 is a plan view of a cuff according to a modification of the present invention.

FIG. 15 is a plan view of a cuff according to a modification of the present invention. Each of hook surface and loop surface illustrated in FIG. 4 is formed by cutting out from roll member. Instead of this method, a combination of hook surface and loop surface may be configured by socalled "hook-and-loop coexisting fastener member". Hook-and-loop coexisting fastener member is a hook-and-loop fastener whose hooks and loops are aligned in predetermined proportion on a sheet of fastener surface. For example, hook surface 43 can be arranged on one side of the hook-and-loop fastener and loop surface 51 can be arranged on the other side of the hook-and-loop fastener as illustrated in FIG. 15. Hook surface and loop surface may also be aligned in a unit of line alternately. Hook surface and loop surface may also be arranged according to a certain area by measuring off hook-and-loop fastener with a certain size. In addition, even if hook-and-loop coexisting fastener is used, when a cuff is fixed to arm, a fixing combination of hook surface and hook surface is included as well as the above embodiment.

When hook-and-loop coexisting fastener is adopted, it is possible to arrange hooks on the peeling start side of the hook-and-loop fastener or provide the hook-and-loop fastener with more hooks than loops on the start peeling side of the fastener surface. It may be acceptable to provide the hook-and-loop fastener with hooks higher than loops. Since hooks and loops are configured as one sheet of fastener surface, it is unnecessary to attach hook surface and loop surface cut out from roll member.

In case of using hook-and-loop coexisting fastener, hook surface and loop surface can be aligned and arranged in smaller unit than in the case of attaching hook surface and loop surface cut out from roll member. Consequently, fastener surface can be optimized against the force vertical to the fastener surface and the shearing force. Also, hard fixing force can be obtained by hook-and-loop coexisting fastener.

Still further, the present invention is by no means limited only to the above embodiment, and can be variously modified in the claims.

Figures 12, 13:
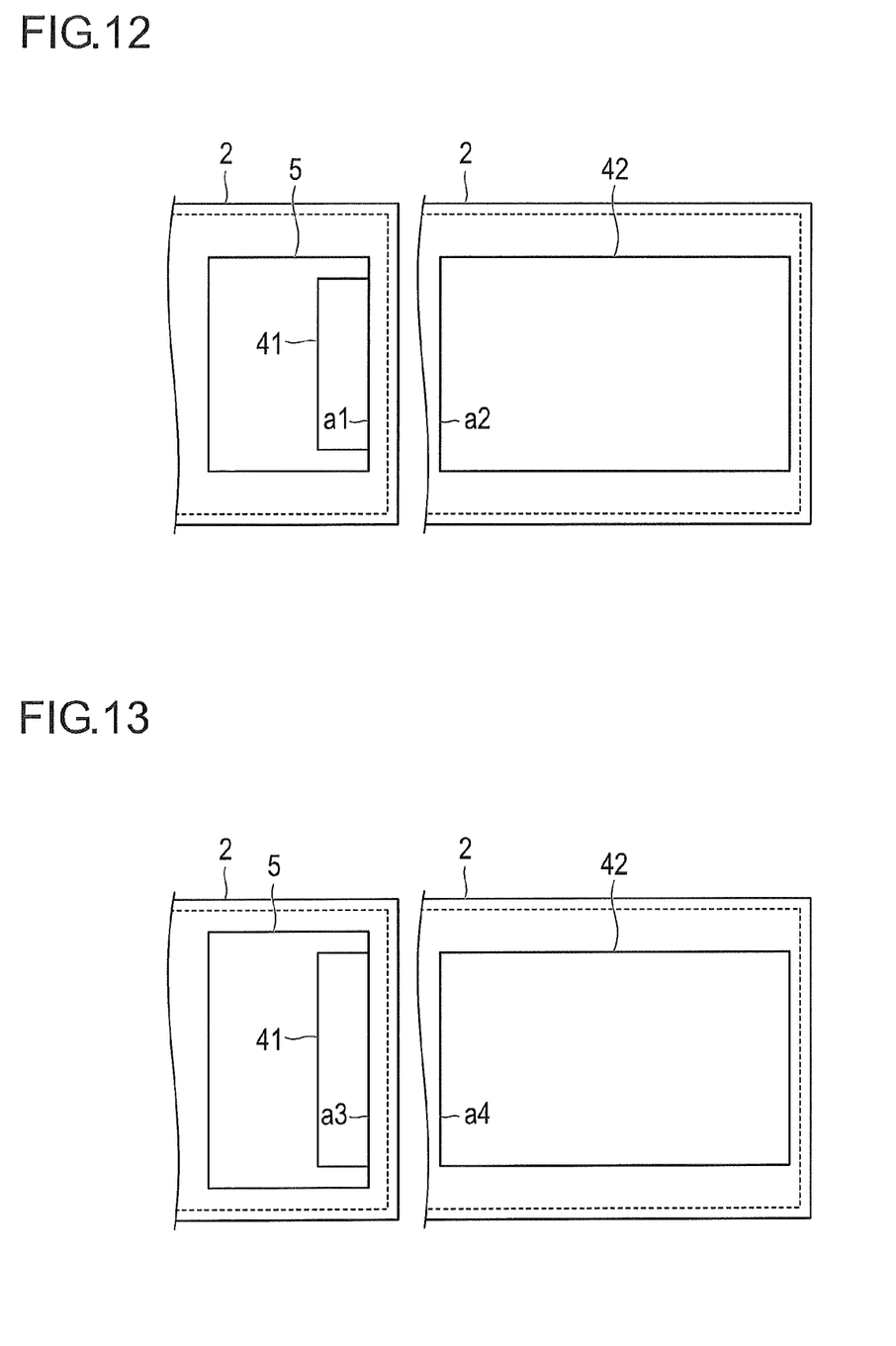
FIG. 12 illustrates an example of a pediatric cuff.
FIG. 13 illustrates an example of an adult cuff.
Figure 14:
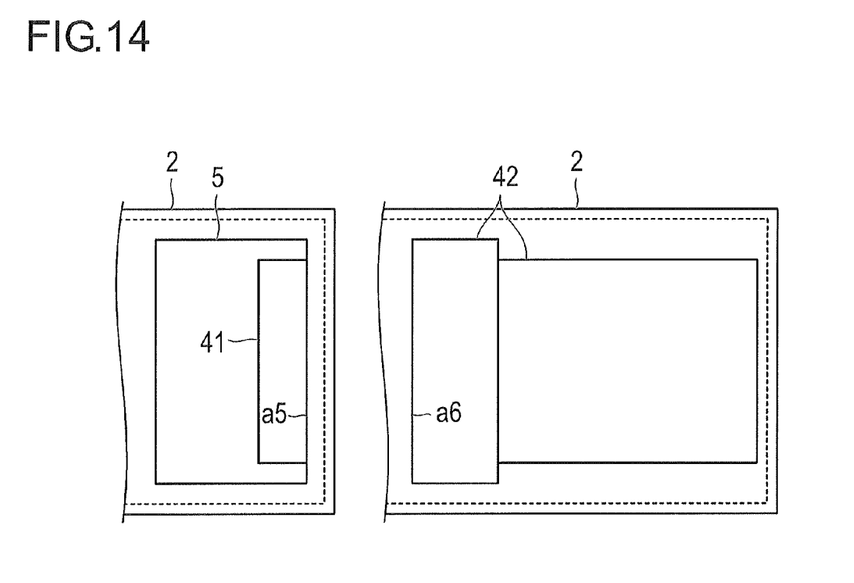
FIG. 14 illustrates an example of a femoral cuff.

FIGS. 12 to 14 are views forming hook surfaces and a loop surface according to a size of the cuff 1 of the embodiment. For example, FIG. 12 illustrates a pediatric cuff, FIG. 13 illustrates an adult cuff and FIG. 14 illustrates a cuff for thigh.

In FIG. 12, a1 and a2 of the cuff 1 oppose to each other upon fixing. In FIG. 13, a3 and a4 oppose to each other upon fixing. In FIG. 14, a5 and a6 oppose to each other upon fixing.

Although the hook-and-loop fastener illustrated in FIGS. 4 and 5 are formed using a conventional roll member in the above embodiment, the present invention is by no means limited to this.

Further, the hook surface 42 and the loop surface 5 are formed to have the same width in the width direction of the body 2 in the above embodiment. However, the present invention is by no means limited to this and each width may be different.

Furthermore, the cuff 1 is configured to include the body 2 and the air bag 3 separately in the above embodiment. However, the cuff 1 may be configured to include the integrated body and air bag.

The entire disclosure of Japanese Patent Application No. 2011-186515 filed on Aug. 29, 2011 including specification, claims, drawings and summary are incorporated herein by reference in its entirety.

The invention claimed is:

1. A blood pressure measuring cuff configured to reduce noise from loosening of the blood pressure measuring cuff, peeling of a hook-and-loop fastener, or friction between an air bag and the blood pressure measuring cuff, comprising:
 a belt-shaped body having a pair of longer edges and a pair of shorter edges shorter than the longer edges, configured to wrap around a blood pressure measuring site of a patient;
 the belt-shaped body comprising a first surface and a second surface, wherein the first surface and the second surface are on opposite sides of the belt-shaped body;
 the first surface comprising a first hook surface having a first hook structure and a loop surface having a loop structure; and
 the second surface comprising a second hook surface having a second hook structure,
 wherein, when the belt-shaped body is configured to wrap around the blood pressure measuring site of the patient, the second hook structure of the second hook surface hooks with the loop structure of the loop surface, while the first hook structure of the first hook surface and the second hook structure of the second hook surface mutually fix each other so as to oppose a shearing force,
 the loop surface has a rectangular shape which is adjacent to one shorter edge of the belt-shaped body,
 the first hook surface is provided on an edge, farthest from the one shorter edge of the belt-shaped body, of the rectangular shape of the loop surface, and
 the loop structure of the loop surface is provided adjacent to the first hook structure of the first hook surface in a width direction of the belt-shaped body.

2. The blood pressure measuring cuff according to claim 1, wherein the first hook structure of the first hook surface is disposed on a part of the loop structure of the loop surface.

3. A blood pressure measuring cuff according to claim 1, wherein the second hook structure of the second hook surface and the loop structure of the loop surface mutually fix each other.

4. A blood pressure measuring cuff according to claim 1, wherein the cuff is used for a blood pressure measurement of a linear inflating scheme in which blood pressure is measured while the cuff is being inflated.

5. A system for measuring the blood pressure of a subject using the measuring cuff according to claim 4, comprising:

a pressure sensor coupled to the measuring cuff for sensing a pressure of a working fluid in the cuff;

a control valve coupled to the measuring cuff;

a pump communicatively coupled to the control valve for pumping the working fluid through the control valve to inflate the cuff;

an indicator for indicating the blood pressure of the subject based on the pressure of the working fluid in the cuff; and a control unit communicatively coupled to the pressure sensor, the control valve, and the pump;

wherein the control unit sends a first control signal to the control valve and a second control signal to the pump responsive to a pressure signal from the pressure sensor, to cause the cuff to be inflated at a substantially constant rate; and wherein the pressure sensor senses the subject's blood pressure through the cuff while the cuff is being inflated, and the control unit generates an indicator signal and sends it to the indicator causing the indicator to indicate at least one aspect of the subject's blood pressure.

* * * * *